(12) United States Patent
Tunnell, Jr. et al.

(10) Patent No.: US 6,419,487 B1
(45) Date of Patent: Jul. 16, 2002

(54) MULTIPORT ANTIBACKFLOW MANIFOLD FOR DENTAL HANDPIECE SYSTEM

(76) Inventors: Vernon R. Tunnell, Jr.; Kimberly D. Tunnell, both of 15223 SE. Clapsop St., Portland, OR (US) 97236

( * ) Notice: Subject to any disclaimer, the term of this patent is extended or adjusted under 35 U.S.C. 154(b) by 0 days.

(21) Appl. No.: 09/705,966

(22) Filed: Nov. 3, 2000

Related U.S. Application Data

(60) Provisional application No. 60/164,127, filed on Nov. 8, 1999.

(51) Int. Cl.⁷ .................................................. A61C 1/02
(52) U.S. Cl. .................................................... 433/98
(58) Field of Search .............................. 433/92, 98, 100

(56) References Cited

U.S. PATENT DOCUMENTS

| | | |
|---|---|---|
| RE30,340 E | 7/1980 | Borden |
| 4,676,750 A | 6/1987 | Mason |
| 4,902,226 A | 2/1990 | Elliott |
| 5,318,443 A | 6/1994 | Overmyer |
| 5,474,451 A | 12/1995 | Dalrymple et al. |
| 5,480,302 A | 1/1996 | Fife |
| 5,551,845 A | 9/1996 | Milam |
| 5,554,025 A | 9/1996 | Kinsel |
| 5,571,412 A | 11/1996 | Nerli |
| 5,716,210 A | 2/1998 | Novak |
| 5,749,726 A | 5/1998 | Kinsel |
| 5,897,317 A | 4/1999 | Hansen |
| 5,961,326 A | 10/1999 | Johnston et al. |
| 5,971,757 A | 10/1999 | Seltzer |
| 6,106,287 A | 8/2000 | Yates |

*Primary Examiner*—Nicholas D. Lucchesi
(74) *Attorney, Agent, or Firm*—Keith A. Cushing

(57) ABSTRACT

An exhaust manifold for a dental handpiece system receives at an inlet thereof return air flow provided by a dental handpiece. A unidirectional valve couples the inlet to a common manifold space which in turn couples to ambient air by way of a filter. By applying filtration on the backside of the unidirectional valve, air entering the common manifold space cannot thereafter reenter the return air conduit and thereby contaminate the same handpiece or other handpieces in a multiple handpiece system. A replaceable filter unit avoids accumulated debris and promotes better sanitary conditions.

10 Claims, 3 Drawing Sheets

MULTIPORT ANTIBACKFLOW MANIFOLD FOR DENTAL HANDPIECE SYSTEM

CROSS-REFERENCE TO RELATED PROVISIONAL APPLICATION

The present application relies for priority of filing on prior-filed provisional application No. 60/164,127 filed Nov. 8, 1999 by the inventors named herein and entitled MULTIPORT ANTIBACKFLOW MANIFOLD WITH SINGLE NOISE REDUCING INFECTION CONTROL DISPOSABLE EXHAUST.

BACKGROUND OF THE INVENTION

As in any medical procedure, dental procedures require strict sanitary conditions guarding against contamination from patient-to-patient or from patient-to-dentist. As patients come and go through a series of examinations and procedures, the dentist must present to each patient sanitary conditions with respect to the environment of the examination and with respect to the equipment used during dental exam and dental procedures. The present invention concerns presentation of both sanitary environment and sanitary equipment to each new patient. More particularly, the present invention concerns dental handpiece systems maintained in sanitary condition and operated in such manner to prevent contamination of the surrounding environment.

Dental handpieces are air-driven devices. A common dental handpiece is the high-speed turbine drill. A turbine drill receives a flow of air along an air supply conduit for application against a rotatable turbine. As the air hits the turbine, it rotates the turbine and thereafter exits the handpiece by way of a return air conduit. Thus, dental handpieces are relatively lightweight devices coupled to a dental handpiece system by way of a set of air conduits. When in use the tool spins at approximately 350,000 rpm and develops a vortex or suction around the tool pulling debris, i.e., blood, saliva, or tooth material, into the handpiece in the vicinity of the turbine. More particularly, typical handpiece construction leaves open the handpiece housing in the vicinity of the turbine bearings. Due to the increased air velocity, and therefore reduced air pressure, debris in the vicinity of the tool moves into the handpiece housing. Accordingly, debris moves into the return air conduit and back into the system delivery unit and eventually into the exhaust system. Because such return air has not traditionally been managed with respect to bio-contamination, such exhaust air typically enters directly back into the ambient air of the dental operating room.

While not well recognized as a significant hazard to patients, dentists, and staff, such untreated release of bio-contaminants represents risk to those in the dental operating room. This becomes especially hazardous where such contaminants remain in place for long periods resulting in growth of hazardous mold and fungus. Thus, contamination becomes serious when debris collected by the handpieces rests for extended periods within the handpiece system delivery unit. Occasional maintenance or repair requiring opening of the delivery unit exposes the maintenance or repair person to significant biohazard. Without strict attention to proper cleanup procedures, such contamination can spread further into the operating room environment during maintenance, repair, or cleanup. Generally, such accumulated biohazard and resulting mold and fungus represent an undesirable presence in any medical environment.

According to one method of treatment, the return air tubes connect together to a common discharge and the debris collects in a gauze pad. Thus, where this method does collect some of the debris carried away from the procedure site, there remains significant contamination in the form of atomized bio-contaminants not captured in the gauze trap and, therefore, entering the ambient air of the dental examination room. When the gauze impedes airflow from the common discharge, a backpressure exists at the terminal portions, i.e., at the common discharge, and, undesirably, airflow passes in the reverse direction along such return air conduits, i.e., passes in the direction of the handpiece. This represents a significant opportunity for bio-contamination of other handpieces as well as the operating room environment.

A second method filters directly at the handpiece, i.e., places in-line a filter along the both the supply and return air conduit at the handpiece. Unfortunately, this should require a filter change for every use. Also, it must be replaced for every patient, it adds additional weight at the handpiece, and it finds application for only a limited set of handpiece types.

U.S. Pat. No. 5,897,317 issued Apr. 27, 1999 and entitled Dental Handpiece With Disposable Filter Cartridge, shows placement of a filter cartridge at the handpiece for cleaning drive air, water, chip air, and exhaust passing through the handpiece. U.S. Pat. No. 5,716,210 issued Feb. 10, 1998 and entitled Disposable Filter For Dental Handpiece also illustrates an insert placed in line at the handpiece for filtering air and water. U.S. Pat. No. 5,749,726 issued May 12, 1998 and entitled Disposable Point Of Use Filtration Element For Purifying Air And Water Supplies To Dental Handpieces also illustrates an in-line proposition for filtration at a dental handpiece relative to cooling water and cooling air supplies but unrestricted turbine supply and return air.

U.S. Pat. No. RE30,340 reissued Jul. 22, 1980 and entitled Dental Handpiece attempts to avoid collection of bio-contaminants at the handpiece by restricting the fluid outlet from the turbine sufficiently to ensure that a portion of the fluid is exhausted through the turbine bearings and openings in the housing to prevent ergots of foreign matter into the interior. Restricting airflow at the downstream side of the turbine, however, impedes turbine performance and, therefore, impedes overall efficiency of the dental handpiece. Furthermore, this proposition undesirably blows excess air into the patient's mouth.

U.S. Pat. No. 5,318,443 issued Jun. 7, 1994 and entitled Method Of Flushing Disinfecting And Lubricating A Dental Turbine Handpiece illustrates a mechanism by which a handpiece may be flushed clean of contaminants while not in operation. Unfortunately, the proposed solution does not address concerns relating to the collection and discharge of bio-contaminants during operation.

The "saliva ejector", i.e., a separate device pulling by vacuum material from the patient's mouth during a procedure, removes excess fluid from the operating site. This system carries the bulk of material away from the site and is well recognized as a source of potential bio-contamination. Some saliva ejector systems filter the return air and deposit the waste into the public sewer. U.S. Pat. No. 5,571,412 issued Nov. 5, 1996 and entitled Dental Filter Assembly illustrates a filter canister assembly receiving waste from a dental cuspidor.

Filtration systems have also been applied in-line relative to water supply lines. For example, U.S. Pat. No. 5,971,757 issued Oct. 26, 1999 and entitled In-Line Filter System For Dental Instruments illustrates a filter unit placed in-line relative to a water supply line for a dental instrument.

Need remains, however, to improve dental handpiece systems to manage better the relatively smaller volume, e.g., in relation to the saliva ejector system, debris inadvertently collected at the handpiece. More particularly, there remains need to reduce the risk of contamination to the doctor, patient, and staff as a result of debris carried by the dental handpiece and potentially accumulating within the dental handpiece delivery unit.

The present invention addresses this and other concerns with management of bio-contamination relative to dental handpieces and dental handpiece systems.

SUMMARY OF THE INVENTION

In accordance with the present invention, an exhaust manifold for a dental handpiece system receives at an inlet thereof return air flow provided by a dental handpiece. A unidirectional valve couples the inlet to a common manifold space which in turn couples to ambient air by way of a filter. By applying filtration on the backside of the unidirectional valve, air entering the common manifold space cannot thereafter reenter the return air conduit and thereby contaminate the same handpiece or other handpieces in a multiple handpiece system.

As applied in a multiple handpiece system, the exhaust manifold under the present invention includes a plurality of inlets each corresponding to and receiving the return air from a corresponding handpiece. Each inlet in turn couples by way of a corresponding unidirectional valve to the common manifold space. The common manifold space in turn couples to ambient air via a filter. Back pressure produced at the filter relative to the common manifold space cannot reintroduce air back into any of the return air supply conduits because the corresponding unidirectional valves block such air flow.

The filter unit as proposed under the present invention is removeably mounted and thereby replaceable when needed. Frequent replacement of the filter unit protects against undesirable accumulation of bio-contaminants and growth of microorganisms thereupon.

Ambient air within the dental examination area is thereby protected against contamination as well all dental handpieces within a dental handpiece system protected against contamination relative to bio-contaminants and oil originating from a given handpiece.

The subject matter of the present invention is particularly pointed out and distinctly claimed in the concluding portion of this specification. However, both the organization and method of operation of the invention, together with further advantages and objects thereof, may best be understood by reference to the following description taken with the accompanying drawings wherein like reference characters refer to like elements.

BRIEF DESCRIPTION OF THE DRAWINGS

For a better understanding of the invention, and to show how the same may be carried into effect, reference will now be made, by way of example, to the accompanying drawings in which.

DETAILED DESCRIPTION OF THE PREFERRED EMBODIMENT

Figure 1:
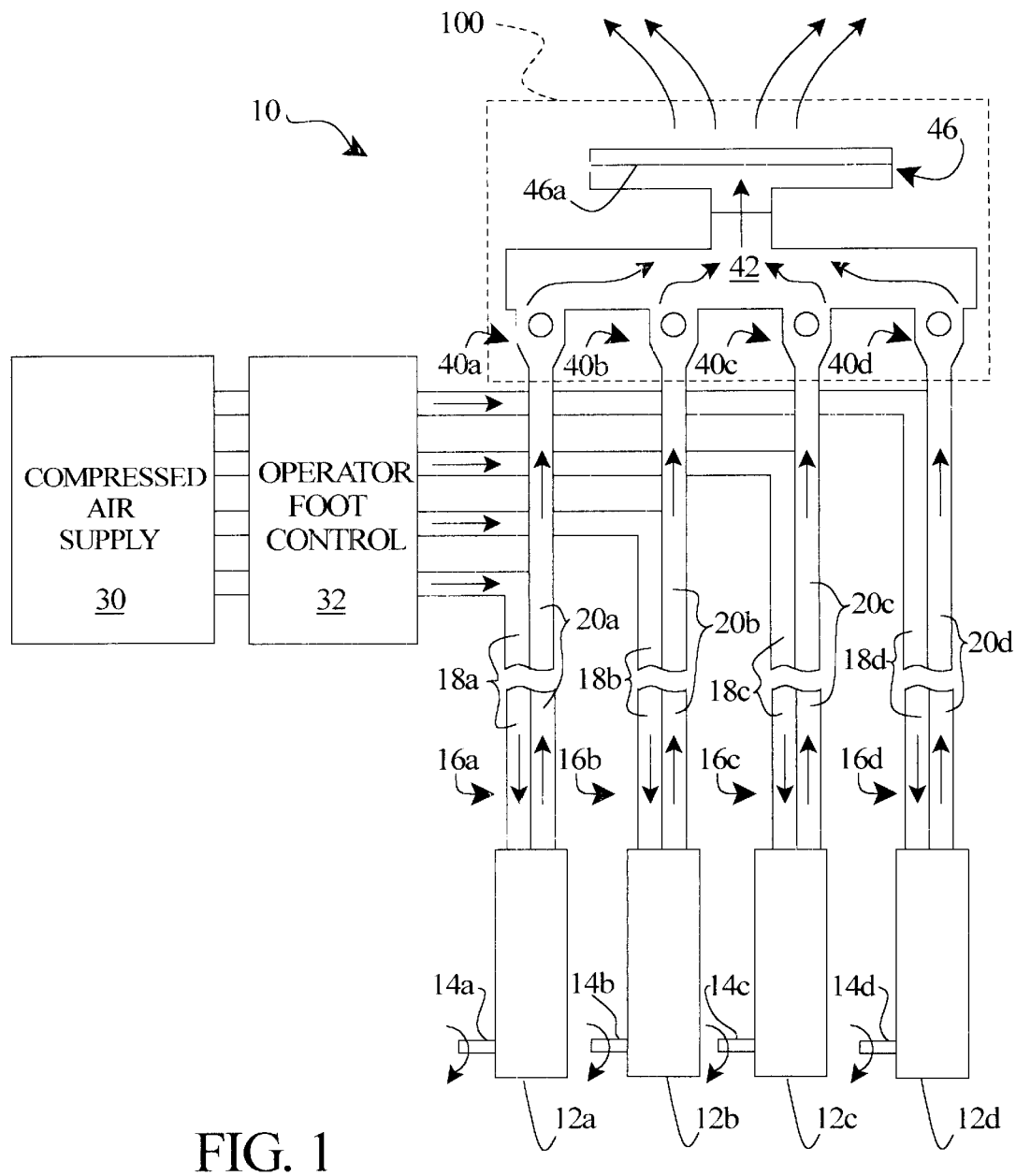
FIG. 1 illustrates schematically a dental handpiece system including a multiport antibackflow manifold according to the present invention.

FIG. 1 illustrates schematically a dental handpiece system 10 according to the present invention. According to one aspect of the present invention, system 10 employs multiple dental handpieces. In the present illustration, four such handpieces will be shown, however, it will be understood that any selected number of handpieces may be utilized under the present invention.

In FIG. 1, system 10 includes a set of handpieces 12, individually handpiece 12a–12d. Each handpiece 12 carries a tool 14, individually tools 14a–14d. In this particular illustration, each handpiece 12 is a high-speed turbine drill rotating the corresponding tool 14 at high speeds, e.g., 350,000 rpm, for purposes of executing dental procedures. Dental handpiece systems include other, i.e., low speed or ultra sonic, handpieces which do not necessarily undesirably collect bio-contaminants during use. However, such other handpieces typically also operate in the fashion illustrated relative to handpieces 12, i.e., receive a flow of supply air and return the supply air through an exhaust system. The present invention is well suited for operation in conjunction with such other handpieces and is especially useful for filtering oil from the return air relative to surrounding ambient air. The present disclosure focuses, however, on the undesirable collection of bio-contaminants by high-speed handpieces such as handpieces 12 illustrated in FIG. 1.

Each handpiece 12 couples to the remainder of system 10 by means of a tubing set 16, individually tubing sets 16a–16d. Each tubing set 16 includes a plurality of conduits. In addition to those illustrated herein, tubing sets 16 include cooling fluid, e.g., cooling air or water, supply and return conduits and the like (not shown herein). As relevant to the present invention, each tubing set 16 includes an air supply conduit 18 and an air return conduit 20, individually air supply conduits 18a–18d and air exhaust conduits 20a–20d. Air forced down a given supply conduit 18 strikes a turbine (not shown) within the corresponding handpiece 12 causing the corresponding tool 14 to rotate at high speed. After striking the turbine, the air travels back to the dental unit (not shown in FIG. 1) along the corresponding return conduit 20.

A compressed air supply 30 couples to each of the air supply conduits 18 by way of an operator foot control 32, e.g., foot operated control. In this manner, an operator selectively introduces air from supply 30 into a selected one of air supply conduits 18 and thereby selectively operates one of handpieces 12.

Each return conduit 20 terminates at a unidirectional valve 40, individually valves 40a–40d. Each valve allows a one-way flow of return air out of the corresponding return conduit 20 and into a common manifold 42. As may be appreciated, air exiting a given return conduit 20 and passing through the corresponding valve 40 into common manifold 42 cannot thereafter reenter any one of return conduits 20 by virtue of the valves 40. In other words, once air enters common manifold 42 it cannot thereafter reenter any conduit 20. Common manifold 42 couples to ambient air space 44 by way of a removable filter unit 46. Filter unit 46 includes a hepa filter element 46a mounted therein. It is suggested, however, that hepa-filter element 46a be permanently mounted within unit 46 and that unit 46 be removably mounted.

As will be appreciated, back-pressure created within common manifold 42 by virtue of filter unit 46 cannot cause air flow back into return conduits 20 by virtue of unidirectional valves 40. Accordingly, once air reaches common manifold 42 it is destined to exit system 10 only by way of filter unit 46.

Debris accumulates at filter element 46a and eventually reaches a given magnitude, filter unit 46 may be replaced, e.g. once-a-week. System 10 thereby protects ambient air space 44 against contamination from oil as originating at compressed air supply 30 or, more importantly, bio-contaminants as carried from the patient by handpieces 12. Filter element 46a provided as a hepa-filter at a 0.1 micron filtration rating eliminates most contaminants, i.e., blood, saliva, bacteria, fungus, pulled into the handpiece by vacuum effect during use thereof or other contaminants passing through the handpiece, e.g. oil from the compressed air supply 30. Filter unit 46 may be disposed of with other bio-hazardous materials from the dental office.

Thus, system 10 addresses contamination control issues in dental operations. By virtue of valves 40, return air cannot pass from one handpiece back into another handpiece. Furthermore, return air must pass through filter element 46a before it enters ambient air space 44. Because filter unit 46 is replaceable, accumulated microorganisms, fungus or mold growing at filter unit 46 need not accumulate at all or beyond undesirable magnitude. System 10 thereby protects doctors, patients and staff against exposure to undesirable bio-contaminants, microorganisms, fungus, and mold in the operating area. In this aspect, system 10 eliminates a source of contamination and health risk for patients, doctors, and staff.

Figure 2:
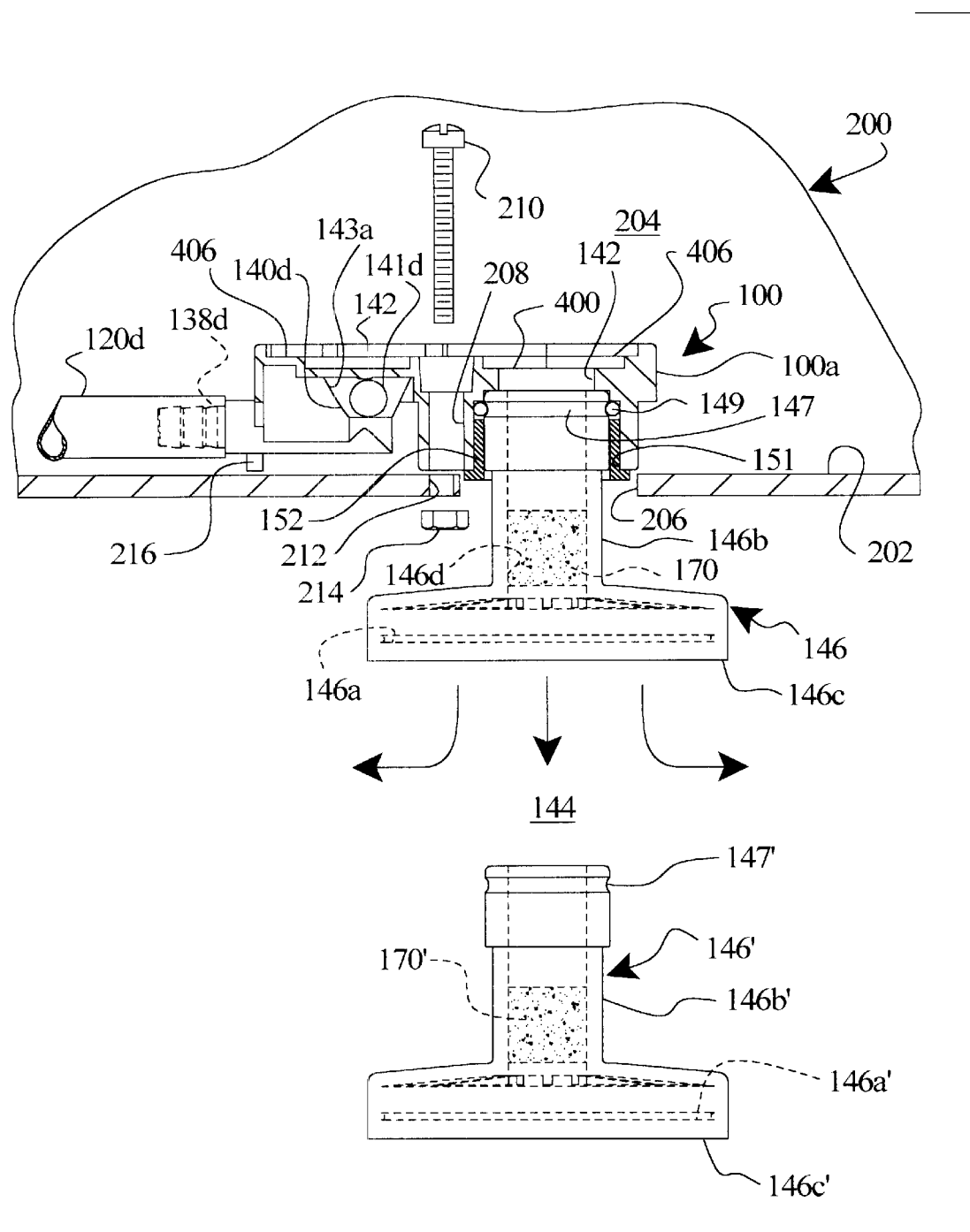
FIG. 2 illustrates a side sectional view of a multiport antibackflow manifold applicable to a pre-existing handpiece system and according to a preferred embodiment of the present invention.

While illustrated in FIG. 1 as an integral part of a dental handpiece system, the present invention may be applied to an existing dental handpiece system by adding a multiport antibackflow manifold 100 as illustrated in FIG. 2. In FIG. 2, the manifold 100 is illustrated in partial sectioned view. Manifold 100 includes a plurality of inlets 138 each communicating with a corresponding ball-type check valve 140. At the downstream side of each valve 140 is the common manifold space 142. At the upstream side is the corresponding inlet 138. FIG. 2 illustrates manifold 100 as mounted to a dental delivery unit 200. The dental delivery unit 200 is an enclosure structure in which the terminal ends of air return conduits 120 may be found. As illustrated in partially broken away view in FIG. 2, unit 200 includes a floor 202 and surrounding wall structures 204. Manifold 100 mounts on the upward facing surface of floor 202 in the vicinity of an opening 206 thereof. The upper portion 100a of manifold 100 includes an opening 208 therethrough. A mounting bolt 210 passes through aperture 208 and a second smaller opening 212 of floor 202 to engage a nut 214 therebelow. A foot 216 extending downward from upper portion 100a also engages in abutment the upward facing surface of floor 202. In this manner, upper portion 100a of manifold 100 finds secure and stable attachment within unit 200 upon floor 202 and in the vicinity of opening 206.

As illustrated in FIG. 2, a filter unit 146 includes a stem portion 146b and a flange portion 146c. A filter element 146a rests within the flange portion 146c of each filter unit 146. Stem 146b includes a central conduit 146d through which air passes and reaches filter element 146a for elimination into the ambient air space 144. Stem portion 146b extends through opening 206 and engages upper portion 100a. In this manner, manifold 100 mounts within unit 200 but leaves external thereof the flange portion 146c. Filter unit 146 may be easily withdrawn from upper portion 100a when sufficient time has elapsed or contaminants accumulated. A replacement filter unit 146' may then be mounted to upper portion 100a of manifold 100.

Each ball-type check valve 140 includes a corresponding ball 141 resting within a conical depression 143. Any airflow through a given valve 140 in the direction of the corresponding inlet 138 immediately drives ball 141 into the well of depression 143 thereby blocking further airflow. Thus, each valve 140 is a unidirectional valve permitting airflow only in the direction from an inlet 138 into manifold 100. As may be appreciated, a variety of unidirectional valve devices may be used.

Each filter unit 146 includes at its proximal end an annular indent 147. An O-ring 149 rests in an opening 151 of upper portion 100a. More particularly, a sleeve 152 captures O-ring 149 within an opening 15 of upper portion 100a. Sleeve 152 permanently attaches to portion 100 and creates in conjunction with opening 151 an annular groove holding O-ring 149. Stem 146a at its proximal end passes through sleeve 152 and engages at its annular indent 147 the O-ring 149. This secures filter unit 146 to upper portion 100a of manifold 100 and also establishes an air tight seal therebetween. Thus, air entering the interior or common manifold area 142 of manifold 100 passes out of upper portion 100a only by way of filter unit 146 and eventually out of filter unit 146 only by way of filter element 146a thereof.

Figure 3:
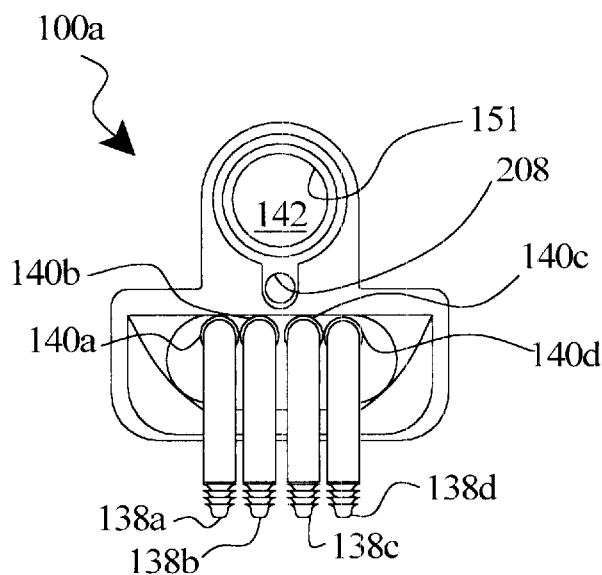
FIGS. 3 and 4 illustrate bottom and top views, respectively, of an upper portion of the manifold of FIG. 2.

FIG. 3 illustrates a bottom view of upper portion 100a only. FIG. 3 illustrates opening 151 in portion 100a without the sleeve 152 attached therein. As best seen in FIG. 3, common manifold space 142 exists at the terminal portion of opening 151 and provides fluid communication with the remainder of common manifold space 142. FIG. 3 also illustrates each of the four inlets 138, individually 138a–138d, for manifold 100. Each inlet 138a communicates with a corresponding one of the ball-type check valves 140, individually 140a–140d. FIG. 3 also illustrates opening 208 passing through upper portion 100a and permitting attachment to floor 202 as illustrated in FIG. 2.

Figure 4:
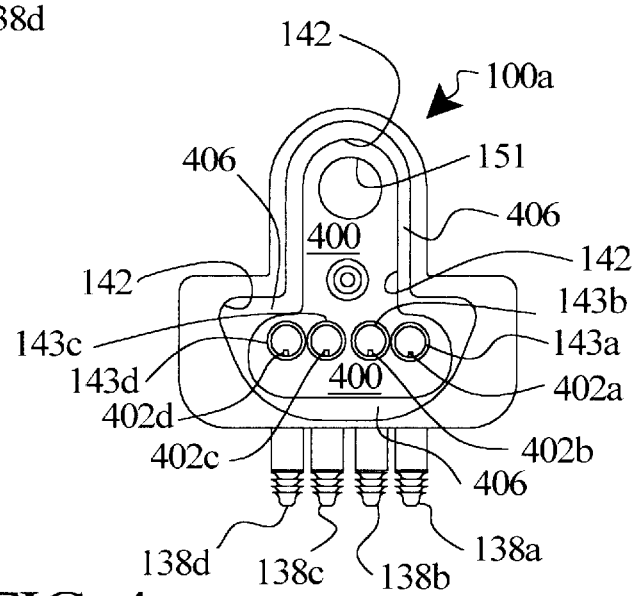

FIG. 4 illustrates a top view of upper portion 100a with a cover 500 (FIG. 5) removed from upper portion 100a. As seen in FIG. 4, the conic depressions 143, individually 143a–143d, open at a most-deep plane 400 within portion 100a. At the well of each conic depression 140, a conduit 402, individually 402a–402d, fluidly couples to the corresponding one of inlets 138, individually 138a–138d, respectively. An offset shelf 406 surrounds the periphery of plane 400 and receives cover 500 (FIG. 5) thereon. Cover 500 captures balls 141 (not shown in FIG. 4) within depressions 143 as well as closes and defines a boundary of manifold space 142. Thus, opening 151 fluidly couples by way of manifold space 142 to the conic depressions 143 and, by way of conduits 402, to the inlets 138. With balls 141 in place, however, fluid flow within upper portion 100a is unidirectional, i.e., from inlets 138 into common manifold space 142 and thereafter out through opening 151 and filter unit 146 into ambient air space 144.

Figure 5:
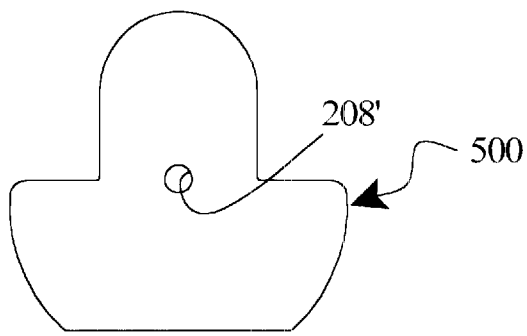
FIG. 5 illustrates a cover for the manifold of FIG. 2.

FIG. 5 illustrate cover 500 including an aperture 208' corresponding in position to aperture 208 of upper portion 100a. Cover 500 attaches to and seals relative to shelve 406 (FIG. 4).

FIG. 2 also illustrates placement of sound suppression element 170 within the conduit 146d of unit 146. Element 170 may be provided as a piece of open-cell foam admitting passage of air therethrough and suppressing sound emanation, e.g., exhaust and ball 141 rattle, from manifold 146.

Slow speed handpieces as well as ultrasonic devices all typically couple into the same exhaust system. Such slow piece devices and ultrasonic devices don't collect significant bio-contaminants but they do carry oil in the return line. These devices can operate on the same exhaust manifold of the present invention to prevent oil contamination of the environment.

It will be appreciated that the present invention is not restricted to the particular embodiment that has been described and illustrated, and that variations may be made therein without departing from the scope of the invention as found in the appended claims and equivalents thereof.

What is claimed is:

1. An exhaust manifold for a dental handpiece system, the exhaust manifold comprising:
   an inlet receiving a return airflow;
   a common manifold space;
   a valve coupling said inlet and said common space and allowing only unidirectional movement of said return airflow from said inlet to said common space; and
   a filter coupling said common space and ambient air space, said common manifold space being otherwise isolated relative to said ambient air space.

2. The system according to claim 1 wherein said filter is removably mounted on said exhaust manifold.

3. The system according to claim 1 wherein said valve is a ball-type valve.

4. The system according to claim 1 wherein said filter is a hepa-filter.

5. The system according to claim 1 wherein said filter operates to filter on the order of 0.1 micron.

6. An exhaust manifold for a dental handpiece system, the exhaust manifold comprising:
   a plurality of inlets, each inlet receiving a return air flow;
   a common manifold;
   a plurality of unidirectional valves corresponding to said plurality of inlets, each valve coupled to its corresponding inlet and permitting unidirectional air flow from the corresponding inlet into said common manifold; and
   a filter coupling said common manifold to surrounding ambient air.

7. The manifold according to claim 1 wherein said filter is removably mounted and thereby replaceable with a second filter.

8. The manifold according to claim 1 wherein at least one of said plurality of valves is a is a ball-type valve.

9. The manifold according to claim 1 wherein said filter includes a hepa filter element.

10. The manifold according to claim 1 wherein said filter operates to filter on the order of 0.1 micron.

* * * * *